(12) United States Patent
Hommeltoft et al.

(10) Patent No.: US 7,087,803 B2
(45) Date of Patent: Aug. 8, 2006

(54) METHOD FOR THE RECOVERY OF PERFLUORINATED SULPHONIC ACID

(75) Inventors: Sven Ivar Hommeltoft, Hillerød (DK); Ole Stahl, Lynge (DK)

(73) Assignee: Haldor Topsoe A/S, Lyngby (DE)

( * ) Notice: Subject to any disclaimer, the term of this patent is extended or adjusted under 35 U.S.C. 154(b) by 485 days.

(21) Appl. No.: 10/673,372

(22) Filed: Sep. 30, 2003

(65) Prior Publication Data

US 2004/0082826 A1 Apr. 29, 2004

(30) Foreign Application Priority Data

Oct. 25, 2002 (DK) .................... PA 2002 01622

(51) Int. Cl.
- C07C 2/54 (2006.01)
- C07C 2/56 (2006.01)
- B01D 11/04 (2006.01)
- B01J 38/48 (2006.01)

(52) U.S. Cl. .................. 585/730; 585/712; 585/719; 203/29; 502/31; 526/201

(58) Field of Classification Search .............. 203/29; 502/31; 526/201; 585/712, 719, 730
See application file for complete search history.

(56) References Cited

U.S. PATENT DOCUMENTS

| 5,220,095 A | 6/1993 | Hommeltoft et al. |
| 5,245,100 A | 9/1993 | Hommeltoft et al. |
| 5,472,921 A * | 12/1995 | Hommeltoft ............ 502/31 |
| 5,498,820 A | 3/1996 | Hommeltoft |
| 5,603,812 A * | 2/1997 | Hommeltoft ............ 203/29 |
| 5,759,357 A * | 6/1998 | Hommeltoft ............ 203/29 |
| 6,281,309 B1 * | 8/2001 | Babcock et al. ........ 526/201 |
| 6,340,414 B1 | 1/2002 | Hommeltoft |

FOREIGN PATENT DOCUMENTS

EP 1 044 963 A1 10/2000

* cited by examiner

*Primary Examiner*—Walter D. Griffin
*Assistant Examiner*—Prem C. Singh
(74) *Attorney, Agent, or Firm*—Dickstein Shapiro LLP

(57) ABSTRACT

Method for the recovery of a perfluorinated sulphonic acid from a viscous organic residue by aqueous extraction of the acid from the residue in presence of a solvent containing aromatic compounds.

7 Claims, No Drawings

METHOD FOR THE RECOVERY OF PERFLUORINATED SULPHONIC ACID

FIELD OF THE INVENTION

The present invention relates to recovery of spent perfluorinated sulphonic acid and in particular spent perfluorinated sulphonic acid catalyst from residue in alkylation of paraffins with olefins.

BACKGROUND OF THE INVENTION

Perfluorinated sulphonic acids are effective catalysts in the alkylation of a paraffinic feedstock with olefinic alkylation agents such as alkylation of isobutane with propene and butenes as described in U.S. Pat. Nos. 5,220,095, 5,245,100 and 5,498,820. The alkylation process typically produces various amounts of spent acid catalyst. Byproducts formed in the alkylation reaction deactivate the spent acid.

To improve process economy of the processes involving perfluorinated sulphonic acid catalysts it is highly desirable to recover spent acid catalyst and recycle the catalyst in its active form.

Several attempts have been made in the past to recover valuable amounts of spent perfluorinated sulphonic acid catalyst from alkylation residues. U.S. Pat. No. 6,340,414 thus discloses recovery of spent acid by heating and distillation. Recovery of a fluorinated sulphonic acid from a spent acid product by steps of subjecting the spent acid product to thermal treatment to obtain the acid in its active form and a residue and separating the active acid from the residue by stripping with a stripping agent and separating the stripping agent from the active acid by distillation is known from EP-A-1,044,963.

By the above known recovery processes still valuable amounts perfluorinated sulphonic acid is contained in a viscous residue being formed during recovery.

DK PA 2001 00809 discloses a method to treat such viscous residues for the further recovery of acid by adding an alkyl ammonium salt of the acid to be recovered and subsequently extraction of the acid.

Viscosity of the residues increases as the acid is extracted. In some cases the organic part of the residue even solidifies and encapsulates the acid. The method of DK PA 2001 00809 requires therefore vigorous agitation and heating of the residue during extraction of the acid.

SUMMARY OF THE INVENTION

We have observed that addition of a hydrocarbon solvent being rich in aromatic compounds improves aqueous extraction of perfluorinated sulphonic acids from a residue being formed use or recovery of the acids as catalyst in alkylation of paraffins.

Accordingly, this invention provides a method for the recovery of a perfluorinated sulphonic acid from an organic viscous residue by aqueous extraction of the acid from the residue in presence of a solvent mixture, which is rich in aromatic compounds.

Essentially, any hydrocarbon fraction being rich in aromatic compounds is useful in the inventive process. Light cycle oil, which is a by-product from fluid catalytic cracking of heavy oil, is an example of such a hydrocarbon fraction. Another useful hydrocarbon fraction is reformat gasoline. These fractions contain a mixture of hydrocarbons with a substantial amount of aromatic compounds.

DETAILED DESCRIPTION OF THE INVENTION

Spent acid from alkylation of paraffin alkylation in presence of trifluoromethanesulphonic acid was used in the following examples containing about 70% by weight trifluoromethanesulphonic acid and 30% by weight acid soluble oil (alkylation residue). The spent acid was mixed with 20% by weight triethyl ammonium triflate and then stripped in a stripping column with pentane at 250° C. Most of the acid in the spent acid was recovered in the overhead product from this stripping operation. An organic viscous residue was withdrawn from the bottom of the stripping column. The stripping residue was isolated and employed in the following experiments. The residue contained the entire amount of triethyl ammonium triflate and about 10% by weight of the amount of trifluoromethanesulphonic acid contained in the spent acid.

EXAMPLE 1

Extraction of Stripping Residue in Presence of Reformat

The extraction procedure was performed at room temperature and at atmospheric pressure. 35 g of the residue were mixed with 15% by weight reformat and extracted five times with 50 g portions of water by shaking for 30 seconds. An aqueous extract was separated from the residue by centrifugation. The content of recovered trifluoromethanesulphonic acid in each extraction is summarised in Table 1 below.

After five extractions the residue was extracted with diluted NaOH. Substantially no trifluoromethanesulphonic acid was found in the basic extract.

The above procedure was repeated. Results of the second experiment are listed in the Table below.

TABLE 1

| | Extraction of residue with water in the presence of reformat | |
|---|---|---|
| Extraction | 1st experiment % recovery of trifluoromethanesulphonic acid | 2nd experiment % recovery of trifluoromethanesulphonic acid |
| 1 | 95.8 | 91.0 |
| 2 | 3.53 | 7.95 |
| 3 | 0.61 | 0.95 |
| 4 | 0.06 | 0.04 |
| 5 | 0.01 | 0.02 |
| Total extracted | 100.0 | 100.0 |

EXAMPLE 2

Extraction of Stripping Residue in Presence of Light Cycle oil (LCO)

Extraction of the residue was carried out by the same procedure as in the above Example 1. Results from two experiments are summarised in Table 2. NaOH extract in these experiments contained 0.1–0.2% by weight of the total amount of trifluoromethanesulphonic acid contained in the residue.

TABLE 2

| Extraction | 1st experiment % recovery of trifluoromethanesulphonic acid | 2nd experiment % recovery of trifluoromethanesulphonic acid |
|---|---|---|
| 1 | 82.4 | 81.4 |
| 2 | 14.96 | 16.51 |
| 3 | 1.46 | 1.21 |
| 4 | 0.53 | 0.22 |
| 5 | 0.48 | 0.60 |
| Total extracted | 99.8 | 99.9 |

COMPARISON EXAMPLE 3

50 g of the residue were mixed with 50 g water. The extraction was performed at room temperature causing the residue to be solidified, so that extraction and phase separation were not possible.

EXAMPLE 4

Extraction of Residue with Anisole

Residue feed in this experiment did not contain triethylammonium triflate and consisted of trifluoromethane sulphonic acid dissolved in a highly viscous organic residue. The residue was dissolved in anisole (methylphenyl ether, methoxybenzene) to form a 20% solution and 5 g of this solution was extracted with 5 g water by shaking the two phases in a centrifuge glass and subsequently separating the phases by centrifugation. The aqueous phase was separated and the remaining organic phase was subsequently extracted with additional 5 g portions of water. The analysis showed that 70% of the trifluoromethansulphonic acid was extracted in the first extraction, a further 21% were extracted in the second extraction and 5% were extracted in the third extraction. The remaining 4% were extracted in 3 subsequent extractions.

The invention claimed is:

1. Method for the recovery of a perfluorinated sulphonic acid from an organic viscous residue by aqueous extraction of the acid from the residue in presence of a solvent containing one or more aromatic compounds.

2. Method according to claim 1, wherein said solvent comprises an aromatic ether solvent.

3. Method according to claim 2, wherein said aromatic ether is anisole.

4. Method according to claim 1, wherein said solvent is a hydrocarbon solvent containing 20% or more of aromatic hydrocarbons.

5. Method of claim 1, wherein the solvent is reformat gasoline.

6. Method of claim 1, wherein the solvent is light cycle oil.

7. Method according to claim 1, wherein the perfluorinated sulphonic acid is trifluoromethanesulphonic acid.

* * * * *